United States Patent [19]

Jackson

[11] Patent Number: 5,513,634
[45] Date of Patent: May 7, 1996

[54] COMBINATION INTEGRAL BITE BLOCK AIRWAY AND NASAL CANNULA

[75] Inventor: Frank W. Jackson, Mechanicsburg, Pa.

[73] Assignee: Chek-Med Systems, Inc., Camp Hill, Pa.

[21] Appl. No.: 239,195

[22] Filed: May 6, 1994

[51] Int. Cl.[6] .................... A61M 16/00; A61M 15/08; A62B 9/06; A62B 7/00
[52] U.S. Cl. ............... 128/207.18; 128/207.14; 128/912; 128/DIG. 26; 128/200.26
[58] Field of Search .............. 128/200.26, 207.17, 128/207.18, 912, DIG. 26, 207.14

[56] References Cited

U.S. PATENT DOCUMENTS

| | | | |
|---|---|---|---|
| 69,396 | 10/1867 | Brayton et al. | 128/207.18 |
| 718,785 | 1/1903 | McNary | 128/207.18 |
| 1,445,010 | 2/1923 | Feinberg | 128/207.18 |
| 2,931,358 | 4/1960 | Sheridan | 128/207.18 |
| 3,508,543 | 4/1970 | Aulicono | 128/207.18 |
| 3,513,844 | 5/1970 | Smith . | |
| 3,643,660 | 2/1972 | Hudson et al. . | |
| 3,754,552 | 8/1973 | King . | |
| 3,802,431 | 4/1974 | Farr . | |
| 4,263,908 | 4/1981 | Mizerak | 128/205.25 |
| 4,454,880 | 6/1984 | Muto et al. | 128/207.18 |
| 5,174,284 | 12/1992 | Jackson | 128/200.26 |
| 5,269,296 | 12/1993 | Landis | 128/207.18 |
| 5,273,032 | 12/1993 | Borody | 128/200.26 |

OTHER PUBLICATIONS

Oxygenating Mouthguard Alleviates Hypoxia During Gastroscopy, Susan Brandl et al, *Gastrointestinal Endoscopy*, vol. 38, Nov. 4, 1992, American Society for Gastrointestinal Endoscopy.

Photocopy & sketch of prior art device.

Who Is for Supplemental Oxygen?, G. Duncan Bell, M.D., *Gastrointestinal Endoscopy*, vol. 38, Nov. 4, 1992, American Society for Gastrointestinal Endoscopy.

*Primary Examiner*—Kimberly L. Asher
*Attorney, Agent, or Firm*—Eugene Chovanes

[57] ABSTRACT

A combination plastic relatively rigid bite block and soft nasal cannula intended for one-time use for supplying oxygen to a patient's nostrils during an endoscopic procedure. The cannula is fixed into the bite block by an integral clip portion of the cannula extending downwardly from a manifold portion and adhered to the bite block. Flexible nasal prongs extend upwardly from the manifold into the patient's nostrils to supply supplementary gas separately from air breathed through the patient's mouth.

1 Claim, 2 Drawing Sheets

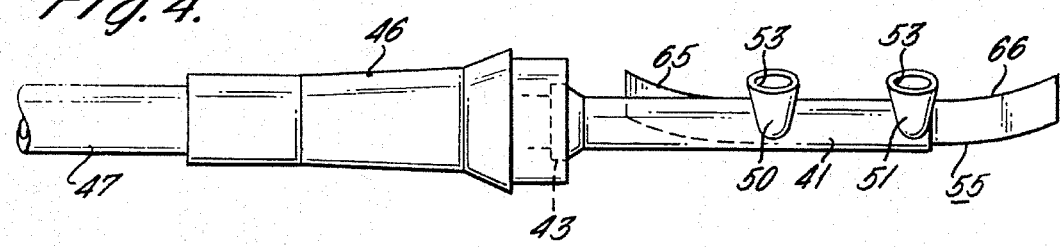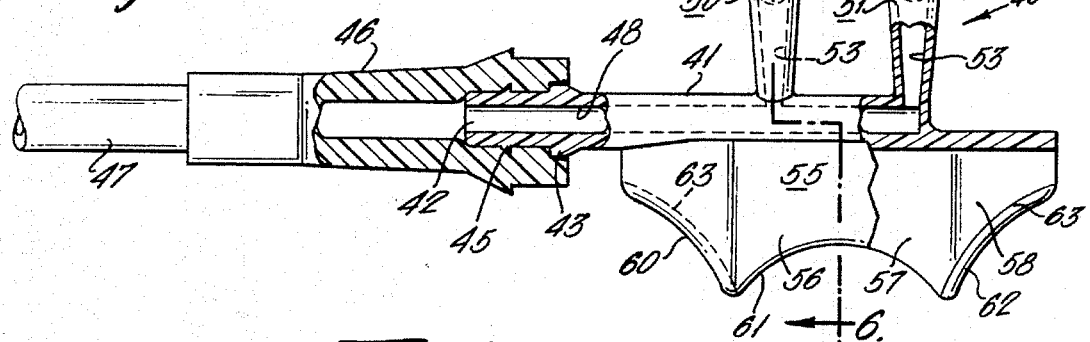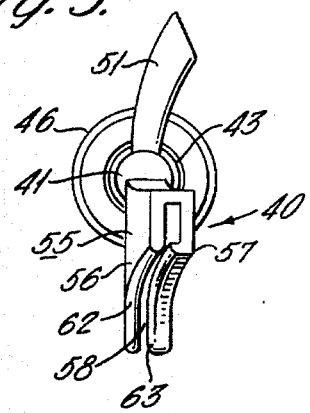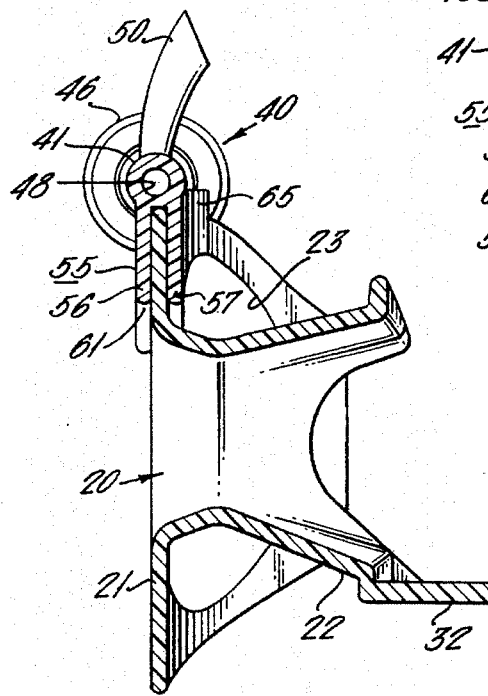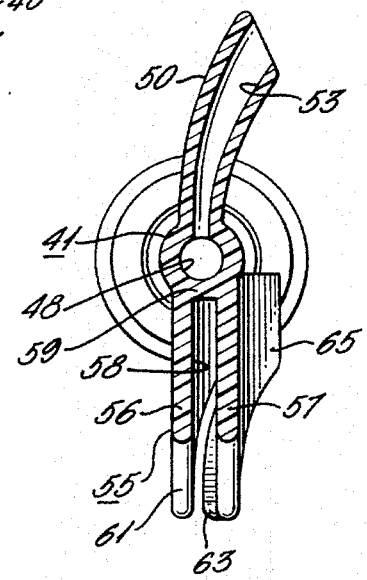

COMBINATION INTEGRAL BITE BLOCK AIRWAY AND NASAL CANNULA

BACKGROUND OF THE INVENTION

Instruments, such as endoscopes, are inserted through a person's mouth into the human body in medical procedures. To prevent the patient from biting into the instrument, a bite block airway is used which is generally basically a rigid plastic tube which is positioned in the patient's open mouth. The instrument is then inserted through the bite block airway or other openings therein into the stomach or other areas.

An example of such a bite block airway is found in my U.S. Pat. No. 5,174,284; the entire disclosure of which is incorporated herein by reference.

During such an endoscopic procedure, the patient is often sedated intravenously. Such sedation generally results in reduced breathing by the patient which in turn reduces the oxygen available to the patient. In order to compensate for such oxygen deprivation, it is standard practice in such endoscopic procedures to administer a supply of a supplementary breathable gas or pure oxygen to patients by using a nasal cannula which usually comprises two prongs extending at generally right angles from a manifold portion having an inlet. A flexible tube connects an oxygen source to the inlet of the cannula. In this way, an adequate supply of oxygen is furnished to the patient.

In the prior art, during such procedures, nasal cannulas were held in place in different ways. Sometimes, the cannulas were taped into place on the patient's face with adhesive tape. Other times, the flexible tube providing the oxygen supply was draped over the patient's ears, as shown for instance in U.S. Pat. No. 3,802,431. Still another alternative was to use a headband attached to the cannula. The band went around the back of the head. In still other instances, the nasal cannula was integrally formed into a face mask as seen in U.S. Pat. No. 4,263,908.

In a more recent development, a standard type plastic endoscopic bite block airway has nasal tunnels formed integrally with the block and extending upwardly to a position below the patient's nostrils whereby an oxygen supply tube could be attached directly to the block with oxygen then being entrained with ambient air and distributed through the tunnels to the nasal passages, or directly into the mouth.

With the nasal cannula separate from the bite block as described above, the taped support or headband support is not totally satisfactory in that the direction of support should be upwards towards the nostrils, whereas the tape and band exert maximum support in a direction inward against the face.

The loops over the ears create an awkward draping of tubes about the patient's head, in the very area where the physician is conducting the procedure on the patient. Again, as with the tape and band, such support is not really firm in the area where support is most needed; namely, right in the area of the nostrils.

Since an integral unit is complex and relatively expensive to mold, it is intended to be reused. Such reuse requires cleaning and sterilization. The integral nasal passages in the form of bores formed into the standard plastic endoscopic bite block have to be vigorously cleaned to prevent contamination and the spreading of infection. Hence, a one-piece cannula and bite block of the prior art had the disadvantage of initial expense and bothersome cleaning and sterilization. Moreover, such integrally molded articles require a compromise between relatively rigid plastics suitable for the bite block and flexible plastic suitable for insertion into the nostrils. Thus, such devices of the prior art required the nasal prongs to terminate below the nostrils due to their relative rigidity.

Advantages of the Invention

The present invention combines the advantages of a separate nasal cannula and a separate bite block since the separate elements can be molded separately relatively simply and economically, and later connected for use, on a one-use, throw-away basis without cleaning and re-sterilization. Of course, the devices can be cleaned, sterilized and re-used if desired.

In addition, the invention eliminates the prior art disadvantages and problems of a separate nasal cannula; namely, support thereof.

Most importantly, the new devices provide the required rigid bite block, but also provide soft resilient nasal prongs for insertion into the patient's nostrils.

SUMMARY OF THE INVENTION

An integral unit is formed that combines the nasal cannula and means which firmly attaches the cannula to a bite block, mechanically, aided by adhesive, thermal fusion or other means. The bite block and airway are rigid but the prongs of the nasal cannula portion are thin and highly flexible, so as not to injure sensitive nasal tissues when inserted into the patient's nostrils.

The nasal cannula has a flexible but relatively stiff horizontal manifold section with an inlet to be attached to an oxygen supply tube. The clip-on mounting portion of the cannula, although molded of flexible plastic is relatively stiff due to the thickness of its walls as compared to the thin-walled nasal prongs.

A structure, preferably bifurcated, extends downwardly from the manifold for engaging the cannula-mounting means of the bite block. This means may have relatively thin-walled webs extending in adjacent flat relationship with a cannula-mounting means of the bite block which preferably fits between the webs.

A cannula is thus formed which is easily and securely attachable by adhesive or otherwise to an upright section of a bite block to provide a secure base for the cannula, thus eliminating any need for any other support such as a headband or the draping of the tube over the patient's ears, or adhesive taping.

The bite block itself is positioned in the patient's mouth by the combination of a headband on the exterior of the head and a portion which extends into the patient's mouth and, as set forth in my U.S. Pat. No. 5,174,284 referred to above, is securely held by the patient who bites on the block during the endoscopic procedure. The prongs of the cannula, which are relatively soft and resilient, are supported upwards, into the patient's nose, in the direction the support is really needed, and not primarily against the face, as often occurred in the prior art. A primary advantage of the present invention is that the bite block and nasal cannula are molded separately from different plastics, each best suited to its element of the combination.

DETAILED DESCRIPTION OF THE DRAWINGS

FIG. 1 is a perspective view illustrating an integrated assembly of the invention that would normally be utilized during an endoscopic examination and which is normally a one-use, throw-away design. The device shown consists of a separately molded bite block and a separately molded nasal cannula fixed together, and a plastic oxygen delivery tube having terminal connectors at both ends, all shown in accordance with the invention.

FIG. 3 is an enlarged fragmentary front elevational view of the cannula taken on the line 3—3 of FIG. 2.

FIG. 4 is a plan view of FIG. 3.

FIG. 5 is a side elevational view of FIG. 3 as viewed from the right-hand side of FIG. 3.

FIG. 6 is an enlarged transverse sectional elevational view taken on the line 6—6 of FIG. 3.

FIG. 7 is an enlarged transverse sectional elevational view taken on the line 7—7 of FIG. 1.

DESCRIPTION OF THE PREFERRED EMBODIMENT

Figure 1:
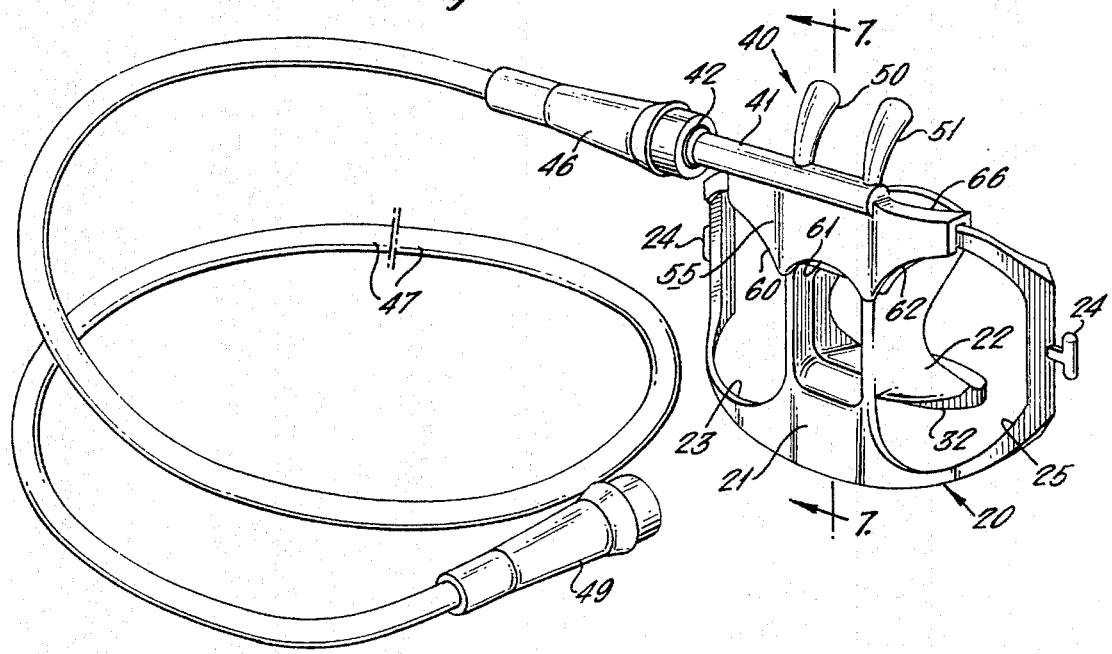

A bite block 20 of a prior art type as described for instance in my U.S. Pat. No. 5,174,284, has a front piece 21 and an airway channel 22 extending rearwardly therefrom, with an optional tongue depressor 32 positioned at the back of the airway channel. Front piece 21 is intended to extend around the front of a patient's open mouth over the lips. The front piece 21 has side openings or ports 23 and 25 for insertion of instruments. Resilient side portions of the front piece 21, carry anchors 24 in T-form for attachment of an elastic headband, not shown, that extends around the back of the head to hold the bite block in place. Holes in the headband provide adjustability. The T-anchors 24 pass through selected holes in the headband in the well known manner. The bite block is molded from polystyrene or another suitable plastic.

The bite block 20 rests firmly in a patient's mouth.

The preferred clip-on, adhered, nasal cannula of the present invention is designated 40 in the drawings. The cannula 40 has a manifold section 41 having an inlet at 42. Inlet 42 has shoulder portions 43 and 45 adapted to receive tubing connector 46 of a suitable flexible plastic. Connector 46 is adhesively or otherwise secured to a flexible plastic oxygen supply tube 47, which is secured with connector 49 to a suitable source of oxygen under pressure in the well known manner.

Cannula 40 has therein bore 48 which extends through the manifold 41 to lateral nasal prongs 50 and 51. Prongs 50 and 51 have a gradual outward flair 52 with corresponding outwardly flaring interior bores 53. The entire nasal cannula 40 is intended to be molded of a suitable flexible plastic such as a styrenic block copolymer by, for instance, injection molding. It is important to the invention that the entire cannula, though molded in one piece, has portions thereof of different degrees of flexibility. Of the portions described so far, the manifold portion is desirably flexible but relatively stiff so as to form a base for the prongs. The nasal prongs are desirably much softer and more flexible than the manifold, so that they are comfortable to the patient when the cannula is in use with these prongs inserted in the nostrils. The difference in relative stiffness and flexiblity between the manifold and lower or clip-on portions of the cannula and the highly flexible nasal prongs is achieved by heavier and thinner walls, respectively.

The combination bite block and cannula is normally intended to be used once, and then thrown away, so that subsequent cleaning and sterilization becomes unnecessary. Hence, the plastic materials should be of relatively inexpensive types such as are commonly used in containers or other inexpensive commodities.

Formed integrally with the manifold and prong portions of the cannula described is a clip portion 55. Clip portion 55 has walls or webs 56 and 57 extending downwardly, relatively close and parallel to one another, to form an interior slot 58. In cross section as seen, for instance, in FIG. 6, clip portion 55 is in inverted U-shape with the base of the U integral with manifold 41 and the arms of the U extended downwardly.

The clip portion 55 of the cannula 40 when viewed from the front as in FIG. 3, has suitable cutouts in the form of arcs as at 60, 61 and 62. These arcs conform to ports 23 and 25 of the front piece 21 of bite block 20. Webs 56 and 57 also have a curvature at 65 and 66 when viewed from above as seen in FIG. 4. Again, this curvature conforms to the curvature of front 21 of bite block 20. Webs 56 and 57 also have a slight bead 63 extending around the periphery of the interior walls of the webs at the lower arc portions 60, 61 and 62. Webs 56 and 57 are integrally formed as by, for instance, injection molding with the manifold and prong portions 50 and 51 but have walls of intermediate thickness so that the webs 56 and 57 in U form are in effect a springy clip, whereas base 59 which is thicker is relatively stiff. Thus, cannula 40 is integrally formed essentially of a flexible but stiff manifold, an integral springy, flexible clip portion 55, and a pair of relatively flexible, soft prongs.

Figure 2:
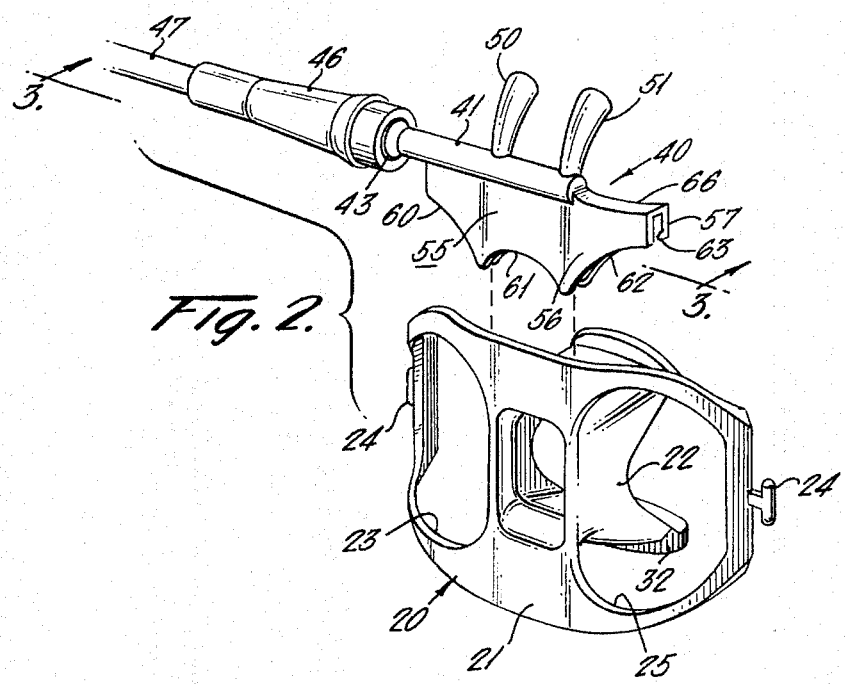
FIG. 2 is an exploded perspective view illustrating the nasal cannula separate from the bite block prior to assembly as in FIG. 1.

In use, cannula 40 is positioned over bite block 20 as seen in FIG. 2 and then forced downwardly to clip on to the bite block 20, and specifically front 21, as seen in FIG. 1.

Although the clip-on portion of the cannula is relatively stiff as compared to the nasal prongs, and has sufficient strength to support those prongs, it still requires a connection to the bite block by firm bonding means such as an adhesive, thermal or other bonding.

Where prongs 50 and 51 are inserted into the patient's nostrils and the structure is in operable position, the oxygen supply tube 47 is connected to a source of oxygen and a flow takes place continuously through the tube into the cannula 40, through bore 48, and into nasal prongs 50 and 51, through the outward flaring bores, thus introducing a supplementary gas, usually oxygen, directly to the patient without entraining ambient air therewith.

It will be obvious to those skilled in the art that the invention has been described in connection with a preferred embodiment shown in the drawings and that other embodiments are contemplated within the scope of the claims.

I claim:

1. A combined and integral endoscopic bite block and nasal cannula arrangement comprising:

a) a bite block assembly having an airway adapted to introduce ambient air into a patient's mouth, and a nasal cannula arrangement mounting member extending upwardly above said airway;

b) a nasal cannula arrangement having a manifold adapted to receive a supplemental gas, a pair of resilient nasal prongs adapted to extend into a patient's nostrils, said nasal prongs delivering a supplemental gas, and a downwardly extending member that engages said mounting member of said bite block, said nasal cannula arrangement being fixedly mounted above said bite block airway; and c) means for improving comfort and for preventing nasal tissue damage comprising said bite block assembly being molded from a relatively rigid plastic, the nasal cannula arrangement being molded from a relatively flexible plastic, and said manifold and mounting member of said nasal cannula arrangement having relatively thick walls so as to have adequate structural strength and said nasal prongs having relatively thin walls, and being soft and flexible.

* * * * *